US010842721B2

(12) United States Patent
Lei et al.

(10) Patent No.: US 10,842,721 B2
(45) Date of Patent: *Nov. 24, 2020

(54) PURIFIED POLYUREA CAPSULES, METHODS OF PREPARATION, AND PRODUCTS CONTAINING THE SAME

(71) Applicant: International Flavors & Fragrances Inc., New York, NY (US)

(72) Inventors: Yabin Lei, Holmdel, NJ (US); Li Xu, Newark, NJ (US); Carol Joyce, Toms River, NJ (US); Lewis Michael Popplewell, Morganville, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/249,194

(22) Filed: Jan. 16, 2019

(65) Prior Publication Data

US 2019/0142715 A1   May 16, 2019

Related U.S. Application Data

(63) Continuation of application No. 13/968,862, filed on Aug. 16, 2013, now Pat. No. 10,226,405, which is a continuation-in-part of application No. 13/163,320, filed on Jun. 17, 2011, now abandoned, which is a continuation-in-part of application No. 12/883,337, filed on Sep. 16, 2010, now abandoned, which is a continuation-in-part of application No. 12/562,578, filed on Sep. 18, 2009, now Pat. No. 8,299,011.

(51) Int. Cl.

| *A61K 8/11* | (2006.01) |
|---|---|
| *A61K 8/34* | (2006.01) |
| *A61K 8/84* | (2006.01) |
| *A61Q 13/00* | (2006.01) |
| *A61Q 15/00* | (2006.01) |
| *A61Q 19/00* | (2006.01) |
| *A61Q 5/02* | (2006.01) |
| *A61Q 5/12* | (2006.01) |
| *B01J 13/14* | (2006.01) |
| *B01J 13/16* | (2006.01) |
| *B01J 13/20* | (2006.01) |
| *C11D 17/00* | (2006.01) |
| *C11D 3/50* | (2006.01) |
| *A61Q 19/10* | (2006.01) |

(52) U.S. Cl.
CPC ............. *A61K 8/11* (2013.01); *A61K 8/34* (2013.01); *A61K 8/84* (2013.01); *A61Q 5/02* (2013.01); *A61Q 5/12* (2013.01); *A61Q 13/00* (2013.01); *A61Q 15/00* (2013.01); *A61Q 19/10* (2013.01); *B01J 13/14* (2013.01); *B01J 13/16* (2013.01); *B01J 13/20* (2013.01); *C11D 3/505* (2013.01); *C11D 17/0039* (2013.01); *A61K 2800/412* (2013.01)

(58) Field of Classification Search
CPC . B01J 13/14; B01J 13/16; B01J 13/20; C11D 3/505; C11D 17/0039; A61K 8/11; A61K 8/84; A61K 8/34; A61K 2800/412; A61Q 15/00; A61Q 5/12; A61Q 19/10; A61Q 5/02; A61Q 13/00
See application file for complete search history.

(56) References Cited

U.S. PATENT DOCUMENTS

| 3,743,601 A | 7/1973 | Rao |
| 3,963,680 A | 6/1976 | O'Keefe |
| 4,280,833 A | 7/1981 | Beestman |
| 4,428,983 A | 1/1984 | Nehen |
| 4,489,017 A | 12/1984 | Alberts |
| 4,563,212 A | 1/1986 | Becher |
| 4,640,709 A | 2/1987 | Beestman |
| 4,650,769 A | 3/1987 | Kakimi |
| 4,785,048 A | 11/1988 | Chao |
| 4,798,862 A | 1/1989 | Gillis, Jr. |
| 5,164,126 A | 11/1992 | Kalishek |
| 5,225,118 A | 7/1993 | Juang |
| 5,304,448 A | 4/1994 | Keoshkerian |
| 5,324,584 A | 6/1994 | Juang |
| 5,635,211 A | 6/1997 | Nehen |
| 5,705,174 A | 1/1998 | Benoff |
| 5,866,153 A | 2/1999 | Hasslin |
| 5,925,595 A | 7/1999 | Seitz |
| 6,133,197 A | 10/2000 | Chen |
| 6,340,653 B1 | 1/2002 | Scher |
| 6,586,107 B2 | 7/2003 | Klug |
| 6,797,670 B2 | 9/2004 | Kleban |

(Continued)

FOREIGN PATENT DOCUMENTS

| EP | 1693104 A1 | 8/2006 |
| EP | 2298439 A2 | 3/2011 |

(Continued)

OTHER PUBLICATIONS

Dow Plastics—"PAPI 135." Retrieved on Jan. 3, 2017. Retrieved from the Internet <URL: http://msdssearch.dow.com/PublishedliteratureDOWCOM/ dh_003f/0901b8038003f163.pdf>.
Chinese First Office Action dated Jan. 30, 2014 for Application No. CN 201010548980.0.
Office Communication dated Nov. 21, 2018 from U.S. Appl. No. 15/556,111, filed Sep. 6, 2017.
Office Communication dated Jun. 27, 2018 from U.S. Appl. No. 15/675,004, filed Aug. 11, 2017.
Office Communication dated Jan. 7, 2019 from U.S. Appl. No. 15/675,004, filed Aug. 11, 2017.
Office Communication dated Jun. 25, 2015 from U.S. Appl. No. 13/968,862, filed Aug. 16, 2013.

(Continued)

*Primary Examiner* — Doan T Phan
(74) *Attorney, Agent, or Firm* — Licata & Tyrrell P.C.

(57) ABSTRACT

Purified polyurea capsules that encapsulate active materials for use in personal care, fine fragrance, or deodorant products are provided as are methods for producing the same.

13 Claims, 2 Drawing Sheets

(56) References Cited

U.S. PATENT DOCUMENTS

| | | |
|---|---|---|
| 6,964,994 B1 | 11/2005 | Antonietti |
| 7,125,835 B2 | 10/2006 | Bennett |
| 7,632,789 B2 | 12/2009 | Brain |
| 8,026,206 B2 | 9/2011 | Sajic |
| 8,299,011 B2 | 10/2012 | Lei |
| 2002/0079599 A1 | 6/2002 | Kleban |
| 2004/0121155 A1 | 6/2004 | Matsunami |
| 2004/0156742 A1 | 8/2004 | Milan |
| 2005/0153135 A1 | 7/2005 | Popplewell |
| 2005/0153839 A1 | 7/2005 | Tamura |
| 2005/0161843 A1* | 7/2005 | Wang .................. B01J 13/04 264/4.1 |
| 2005/0271735 A1 | 12/2005 | Stover |
| 2007/0042182 A1 | 2/2007 | Markus |
| 2007/0138672 A1 | 6/2007 | Lee |
| 2007/0202063 A1 | 8/2007 | Dihora |
| 2008/0103265 A1 | 5/2008 | Schocker |
| 2008/0131695 A1 | 6/2008 | Aouad |
| 2008/0187596 A1 | 8/2008 | Dihora |
| 2008/0200363 A1 | 8/2008 | Smets |
| 2008/0206291 A1 | 8/2008 | Ouali |
| 2009/0053161 A1 | 2/2009 | Nguyen |
| 2010/0009893 A1 | 1/2010 | Cavin |
| 2010/0086575 A1 | 4/2010 | Dihora |
| 2010/0119679 A1 | 5/2010 | Dihora |
| 2011/0071064 A1 | 3/2011 | Lei |
| 2011/0077188 A1 | 3/2011 | Ouali |
| 2011/0077375 A1 | 3/2011 | Kulke |
| 2011/0230390 A1 | 9/2011 | Ouali |
| 2012/0016139 A1 | 1/2012 | Screen |
| 2012/0148644 A1* | 6/2012 | Popplewell ............. A61K 8/11 424/401 |
| 2013/0109569 A1 | 5/2013 | Dave |
| 2013/0337023 A1 | 12/2013 | Lei |

FOREIGN PATENT DOCUMENTS

| | | |
|---|---|---|
| JP | 5068970 A | 6/1975 |
| WO | 2004098767 A1 | 11/2004 |
| WO | 2006006003 A1 | 1/2006 |
| WO | 2007137441 A1 | 12/2007 |
| WO | 2008031241 A1 | 3/2008 |
| WO | 2009091726 A1 | 7/2009 |
| WO | 2009103615 A1 | 8/2009 |
| WO | 2011154893 A1 | 12/2011 |
| WO | 2012107323 A1 | 8/2012 |
| WO | 2013000587 A1 | 1/2013 |
| WO | 2013059167 A2 | 4/2013 |
| WO | 2013092958 A1 | 6/2013 |

OTHER PUBLICATIONS

Office Communication dated Nov. 18, 2015 from U.S. Appl. No. 13/968,862, filed Aug. 16, 2013.
Office Communication dated Sep. 1, 2016 from U.S. Appl. No. 13/968,862, filed Aug. 16, 2013.
Office Communication dated Mar. 28, 2017 from U.S. Appl. No. 13/968,862, filed Aug. 16, 2013.
Office Communication dated Dec. 19, 2017 from U.S. Appl. No. 13/968,862, filed Aug. 16, 2013.

* cited by examiner

PURIFIED POLYUREA CAPSULES, METHODS OF PREPARATION, AND PRODUCTS CONTAINING THE SAME

INTRODUCTION

This application is a continuation of U.S. patent application Ser. No. 13/968,862 filed Aug. 16, 2013, which is a continuation-in-part of U.S. patent application Ser. No. 13/163,320, filed Jun. 17, 2011, which is a continuation-in-part of U.S. patent application Ser. No. 12/883,337, filed on Sep. 16, 2010, now abandoned, which is a continuation-in-part of U.S. patent application Ser. No. 12/562,578, filed on Sep. 18, 2009, now issued as U.S. Pat. No. 8,299,011, the contents of which are incorporated herein by reference in their entirety.

BACKGROUND

Microencapsulation is used in a variety of different applications where a compound needs to be delivered or applied to a target area, protected from its environment, or released in a time-delayed way or only after a treatment has been applied that triggers release. Various techniques for preparing microcapsules are known in the art and are used, depending on the contents to be encapsulated, the environment in which the microcapsules should retain their integrity and the desired release mechanism.

Interfacial polycondensation is a known technique for preparing microcapsules and versatile microcapsule wall materials are used including polyureas and polyurethanes (WO 2011/154893, WO 2012/107323, US 2011/0077188, U.S. Pat. Nos. 5,635,211, 6,586,107, and 6,797,670). Such wall materials are produced by having a first phase which is water-immiscible and includes a polyfunctional isocyanate, i.e., a diisocyanate and/or a polyisocyanate, and a second aqueous phase that may include a polyfunctional alcohol or amine, i.e., a diol and/or polyol, for obtaining a polyurethane capsule wall or a diamine and/or polyamine having —$NH_2$ and/or —NH groups.

If the active material to be encapsulated is hydrophobic, it will be included in the water-immiscible phase, thereafter the two phases are mixed by high shear mixing to form an oil-in-water emulsion. In this emulsion, the polycondensation reaction will take place. Thus, the small droplets of the water-immiscible phase will be surrounded by the microcapsule wall formed by polycondensation of the isocyanate and the polyalcohol or polyamine as starting materials. Conversely, if the material to be encapsulated is hydrophilic, it will be included in the aqueous phase and the mixture of the two phases converted into a water-in-oil emulsion. The polycondensation reaction will then form microcapsule walls surrounding the droplets of water-miscible phase. Suitable emulsifiers are often utilized to aid in the preparation and stabilization of the emulsion.

Suitable raw materials and processes for preparing microcapsules by polycondensation are described in U.S. Pat. No. 4,640,709 and the literature described therein. As is exemplified therein, and also in U.S. Pat. No. 6,133,197, polyurea and polyurethane microcapsules are often used for rugged applications, such as for encapsulation of agrochemicals, e.g., herbicides and pesticides, where slow time-release is desired to set the agents free. For such applications, the microcapsules also require a relatively high mechanical strength. For the polycondensation reaction, suitable diisocyanate and symmetrical triisocyanate starting materials are disclosed in the prior art.

Polyurea or polyurethane microcapsules have thus far not be applied for the release of benefit agents intended for laundry, washing, cleaning, surface care and personal and skin care. For such applications quicker and easier release and/or less mechanical strength are often desirable. Also, it would be desirable to more precisely influence the capsule wall permeability and other capsule wall properties to achieve the desired release profile and consumer benefits.

SUMMARY OF THE INVENTION

The present invention is a purified polyurea capsule composition and methods for producing the same. In some embodiments, the method involves the steps of preparing an oil phase comprising an active material and at least one polyisocyanate; preparing an aqueous phase comprising at least one polyamine or polyol; emulsifying the oil phase into the aqueous phase to form a fragrance emulsion; adding at least one cross-linking agent to the fragrance emulsion to form a capsule slurry; curing the capsule slurry; and optionally washing the capsule slurry with water until a neutral pH is achieved. In other embodiments, the method involves the steps of mixing a capsule slurry comprising cured polyurea capsules with water; and washing the capsule slurry with the water until a neutral pH is achieved. In certain embodiments, the methods of the invention further include the step of adding a salt to the capsule slurry prior to the step of washing the capsule slurry with water.

This invention also includes formulations containing the purified polyurea capsule composition, a surfactant, water, and optionally an alcohol. Personal care products, fine fragrance, Eau De Toilette products, and deodorant, roll-on or aerosol products containing the purified polyurea capsule composition are also provided.

DETAILED DESCRIPTION OF THE INVENTION

Figure 1:
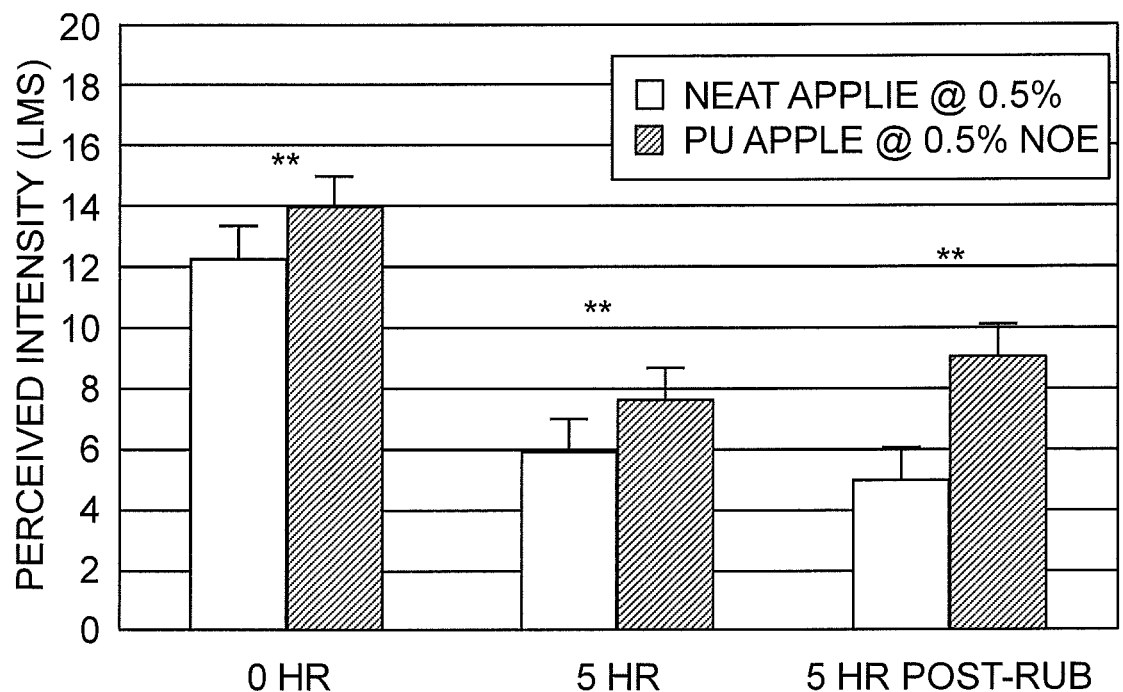
FIG. 1 shows the sensory performance of polyurea (PU) capsules as compared to neat fragrance in a hydroalcoholic aerosole formulation. The perceived intensity is shown using the labeled magnitude scale (LMS). N=14.

It has been found that purified polyurea or polyurethane microcapsules are very suitable for a wide range of consumer applications including personal care products. Specifically, the purified capsules of this invention are particularly well-suited for use in hydroalcoholic medium such as fine fragrance and for use in leave-on personal care applications.

Therefore, this invention is a purified polyurea capsule composition and related process, wherein said purified capsule is composed of an encapsulating polymer and an active material encapsulated by the encapsulating polymer, wherein the encapsulating polymer is the reaction product of polymerization between at least one polyisocyanate, a cross-linking agent and a capsule formation aid.

In one embodiment, purified polyurea capsule compositions of the invention are made by preparing an oil phase containing an active material and at least one polyisocyanate; preparing an aqueous phase containing at least one polyamine or polyol; emulsifying the oil phase into the aqueous phase to form a fragrance emulsion; adding at least one cross-linking agent to the fragrance emulsion to form a capsule slurry; curing the capsule slurry; and washing the capsule slurry with water, e.g., deionized or double deionized water, until a neutral pH is achieved. For the purposes of the present invention, the capsule slurry can be washed using any conventional method including the use of a separatory funnel, filter paper, centrifugation and the like. The capsule slurry can be washed one, two, three, four, five, six, seven, eight, nine, ten or more times until a neutral pH, i.e., pH 7±0.5, is achieved. The pH of the purified capsules can be determined using any conventional method including, but not limited to pH paper, pH indicators, or a pH meter.

A capsule slurry composition of this invention is "purified" in that it is 80%, 90%, 95%, 97%, 98% or 99% homogeneous to polyurea capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the method for preparing purified polyurea capsules includes the additional step of adding a salt to the capsule slurry prior to the step of washing the capsule slurry with water. Exemplary salts of use in this step of the invention, sodium chloride, potassium chloride or bi-sulphite salts.

Given the general applicability of the instant invention for the purification of any capsule, the present invention also provides methods for preparing purified capsules, in particular purified polyurea capsule compositions, by mixing a capsule slurry comprising cured capsules, e.g., polyurea capsules with water; and washing the capsule slurry with the water until a neutral pH is achieved. In one embodiment, this method further includes the step of adding a salt to the capsule slurry prior to the step of washing the capsule slurry with water.

While the following disclosure describes the reactants and encapsulated active materials of particular use in the present invention, this disclosure should not be construed as limiting the method of the invention to only polyurea capsules and flavors/fragrances. It is contemplated that a variety of active material encapsulated microcapsules and can be purified using the method described herein.

Polyisocyanate.

In one embodiment of the invention, the encapsulating wall material of the microcapsule contains one or more isocyanate, polyisocyanate, oligomer, or pre-polymer. In one embodiment of the invention, the microcapsule composition is encapsulated with an encapsulating polymer that contains an isocyanate starting material, wherein this starting material is polyisocyanate, which can be aromatic, aliphatic, linear, branched, or cyclic. As long as the polyisocyanate is water insoluble, it can be used in the current invention. A preferred class of polyisocyanates is an aromatic polyisocyanate that have the generic structure below, and its structural isomer

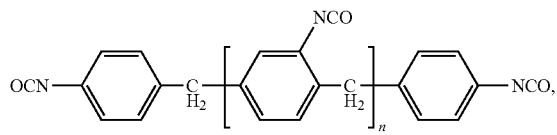

wherein n can vary from zero to a desired number depending on the type of polyamine or polyol used. For the purpose of this invention, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5.

Specific examples of wall monomer isocyanates include, for example, 1,5-naphthylene diisocyanate, 4,4'-diphenylmethane diisocyanate (MOI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanato-cyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, 3,3-bischloromethyl ether 4,4'-diphenyldiisocyanate. Sulfur-containing polyisocyanates are obtained, for example, by reacting 2 mol of hexamethylene diisocyanate with 1 mol of thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

Commercially available polyisocyanates of use in this invention include, but are not limited to, LUPRANATE M20 (BASF), where the average n is 0.7; PAPI 27 (Dow Chemical) where the average n is 0.7; MONDUR MR (Bayer) where the average n is 0.8; MONDUR MR Light (Bayer) where the average n is 0.8; MONDUR 489 (Bayer) where the average n is 1.0; and poly[(phenylisocyanate)-co-formaldehyde] (Aldrich Chemical, Milwaukee, Wis.). Isocyanate monomers such as DESMODUR N3900, DESMODUR N3700, DESMODUR N3600, DESMODUR N3200 and DESMODUR N100 (Bayer Corporation, Pittsburgh, Pa.) may also be used, as well as TAKENATE D110-N(Mitsui Chemicals corporation, Rye Brook, N.Y.).

In general, the average molecular weight of the polyisocyanate in the formulation of this invention varies from 1000 to 250 and preferable from 500 to 275. In general, the range of the polyisocyanate concentration in the composition of this invention varies from 10% to 0.1%, preferably from about 7.5% to about 1%, preferably from about 5% to 0.25%, and most preferably from about 3.5% to about 1.5% of the total capsule suspension.

Isocyanate-based capsule wall technologies are disclosed in PCT 2004/054362; EP 0 148149; EP 0 017 409 B1; U.S. Pat. Nos. 4,417,916, 4,124,526, 5,583,090, 6,566,306, 6,730,635, PCT 90/08468, PCT WO 92/13450, U.S. Pat. Nos. 4,681,806, 4,285,720 and 6,340,653.

Cross Linking Agent.

In another embodiment of the invention, the encapsulating wall material of the microcapsule contains one or more difunctional isocyanates, or isocyanate oligomers, or prepolymers and a cross-linking agent or material, including but not limited to a polyamine, polyol, or combination thereof.

For the purposes of the present invention, the polyamines may be used alone, or mixed together with each other. Water soluble diamine or amine salt or polyamines or polyamines salts are preferred as the amine is usually present in the aqueous phase. Amines useful in the formation of capsules include those compounds containing one or more primary or secondary amine groups which can react with isocyanates or acyl halides to form polyurea or polyamide bonds, respectively. When the amine contains only one amino group, the compound will contain one or more additional functional groups that would form a network through a polymerization reaction. Examples of suitable amines include 1,2-ethylenediamine, 1,3-diaminopropane, 1,4-diaminobutane, 1,6-diaminohexane, hydrazine, 1,4-diaminocyclohexane and 1,3-diamino-1-methylpropane, diethylenetriamine, triethylenetetramine and bis(2-methylaminoethyl)methylamine. Other useful amines include polyethyleneamines $(CH_2CH_2NH)_n$ such as ethyleneamine, diethyleneamine, ethylene diamine, triethylenetetramine, tetraethylenepentamine; polyvinylamines $(CH_2CHNH_2)_n$; polyethyleneimines $(CH_2CH_2N)_x$—$(CH_2CH_2NH)_y$—$(CH_2CH_2NH_2)_z$; polyetheramines; guanidine or guanidine salt; melamine; hydrazine and urea.

Commercially available examples of amines include, but are not limited polyetheramines such as JEFFAMINE EDR-148, JEFFAMINE EDR-176, JEFFAMINE ED Series, and JEFFAMINE TRIAMINES from Huntsman; polyethyleneimines sold by BASF under LUPASOL grades; and polyvinylamines sold by BASF under different LUPAMINE grades. A wide range of polyetheramines may be selected by those skilled in the art. In certain embodiments, the cross-linking agent is hexamethylene diamine, polyetheramine or a mixture thereof.

Polyols of use in this invention generally have at least two nucleophilic centers. For example ethylene glycol, hexylene glycol, pentaerythritol, glucose, sorbitol, and 2-aminoethanol can be used in the preparation of the capsules of this invention.

In general, the range of cross-linking agent concentration or the total amine concentration in the microcapsule composition varies from 5% to 0.1%, preferably from about 2% to about 0.25%, most preferably from about 1 to about 0.5% of the total capsule suspension.

By adding excess amount of polyamine, it has been observed that polyurea formation is driven toward completion thereby reducing the amount of residual polyisocyanate. The reaction stoichiometry requires one amine group per one isocyanate group. By way of illustration, when combining LUPRANATE M20 (having a molecular weight of 360 and isocyanate functionality of 2.7) and hexamethylenediamine (HMDA; having a molecular weight of 116.21 and amine functionality of 2), the stoichiometry of the system indicates that for each gram of HMDA, 2.23 grams of LUPRANATE is needed. The amount of amine will be in excess if more than one gram of HMDA is used per 2.23 grams of LUPRANATE M20. Using a cross-linker in accordance with this invention, residual isocyanate amounts are reduced by at least 30%.

In one embodiment of the invention, the cross linking agent, e.g., hexamethylene diamine, is added to the microcapsule reaction at a temperature of 35° C. In another embodiment, the cross linking agent is added to the microcapsule reaction at a temperature of 22° C.

Capsule Formation Aid.

In another embodiment of the invention, a microcapsule composition is provided that contains an active material that is encapsulated by a polyurea polymer, which are reacted in the presence of a capsule formation aid, e.g., a dispersant or processing aid. For the purpose of this invention, capsule formation aids improve the performance of the microcapsule system. Performance is measured by the intensity of the fragrance release during the pre-rub phase and post-rub. The pre-rub phase is the phase when the microcapsules have been deposited on the cloth, e.g., after a fabric softener containing microcapsules has been used during the wash cycle. The post-rub phase is after the microcapsules have been deposited and the capsules are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide, and ethylene oxide, polyvinylpyrrolidone, polyvinyl alcohols, fatty acid esters of polyoxyethylenated sorbitol and sodium dodecylsulfate. In general, the range of capsule formation aid concentration in the microcapsule composition varies from 4% to 0.5% and preferable from 2% to 1%.

Commercially available capsule formation aids include, but are not limited to, sulfonated naphthalene-formaldehyde condensates such as MORWET D425 (Akzo Nobel); partially hydrolyzed polyvinyl alcohols such as MOWIOLs, e.g., MOWIOL 3-83 (Air Products); ethylene oxide-propylene oxide block copolymers or poloxamers such as PLURONIC, SYNPERONIC or PLURACARE materials (BASF); sulfonated polystyrenes such as FLEXAN II (Akzo Nobel); and ethylene-maleic anhydride polymers such as ZEMAC (Vertellus Specialties Inc.).

Processing aids can include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly (vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly (acrylic acid-co-maleic acid) copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

The capsule formation aid may also be used in combination with carboxymethyl cellulose and/or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. The amount of surfactant present in the capsule slurry can vary depending on the surfactant used. In some embodiments the amount of surfactant is in the range of 0.05 to 0.2 weight percent, in particular when CTAC is employed. In another embodiment, the amount of surfactant is in the range of 1 to 3 weight percent when a saponin or gum arabic is used.

When combined with carboxymethyl cellulose (also referred to as CMC), the lighter color polyvinyl alcohol, carboxymethyl cellulose is preferred. According to the invention, the carboxymethyl cellulose polymer may be represented by the following structure:

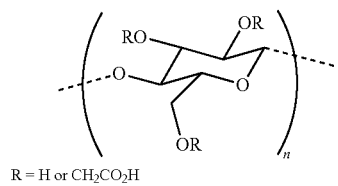

R = H or CH$_2$CO$_2$H

In certain embodiments, the carboxymethyl cellulose polymer has a molecular weight range between about 90,000 Daltons to 1,500,000 Daltons, more preferably between about 250,000 Daltons to 750,000 Daltons and most preferably between 400,000 Daltons to 750,000 Daltons. The carboxymethyl cellulose polymer has a degree of substitution between about 0.1 to about 3, more preferably between about 0.65 to about 1.4, and most preferably between about 0.8 to about 1.0.

The carboxymethyl cellulose polymer is present in the capsule slurry at a level from about 0.1 weight percent to about 2 weight percent and more preferably from about 0.3 weight percent to about 0.7 weight percent.

In some embodiments, CMC-modified microcapsules may provide a perceived fragrance intensity increase of greater than about 15%, and more preferably an increase of greater than about 25% as compared to microcapsules not including CMC.

Additional Polymers.

In addition to the polyisocyanate, cross-linking agent, the encapsulating polymer can also include one or more additional polymers. Additional polymers that can be added to the wall at the formation of the capsules include, e.g., polyamines (polyethyleneimine, poly vinyl amines, etc.), polyacrylates and polyquaterniums. In certain embodiments, the additional polymers may be selected from, but is not limited to, amphoteric and cationic polymers having a molecular weight in the range of from 1,000 to 1,000,000, preferably from 10,000 to 500,000, and most preferred between 100,000 to 200,000.

Examples of amphoteric and cationic polymers include, but not limited to, polyquaternium (e.g., polyquaternium-6 commercially available as MERQUAT 100, polyquaternium-47 commercially available as MERQUAT 2001) and polyvinylamine and its copolymers with vinylformamide and mixtures thereof. Polyvinylamines are polymers which are prepared by acidic or alkaline hydrolysis of poly(N-vinylformamides), as described, e.g., by Gu, et al. ((2002) *J. Appl. Pol. Sci.* 86:3412-3419). The corresponding products are produced in various molecular weights by BASF AG under the trade name "LUPAMIN". These products are used on a large scale, for example, as paper chemicals, in the personal care sector, as super-absorbents or dispersants. The LUPAMIN commercial products still contain the salts formed from the hydrolysis. For the application sector described, the modification of waveguide surfaces, both the salt-containing and the desalinified form can be used. The desalinification can be effected, for example, by ultrafiltration. In a preferred embodiment the polyvinylamine is LUPAMIN 9095 (polyvinylamine PVAm 340,000 g/mol) commercially available from BASF.

In some embodiments, the encapsulating polymer contains from 0.01 to 20 weight percent of the additional polymer, on a solid basis. In other embodiments, the encapsulating polymer contains from 0.1 to 10 weight percent of the additional polymer, on a solid basis. In particular embodiments, the additional polymer is polyquaternium-6 and is present, on a solid basis, in the range of 0.25 to about 10 weight percent. In a further embodiment, the polymer is a mixture of polyquaternium-6 and a polyvinyl amine, specifically LUPAMIN 9095, wherein the polyquaternium-6 may be present, on a solid basis, in the range of preferably 0.5 to 5 weight percent and the polyvinylamine present, on a solid basis, from about 0.25 to 10 weight percent. In still a further embodiment, the additional polymer is a mixture of polyquaternium-6 and polyvinylamine wherein the polyquaternium-6 is present, on a solid basis, in the range of preferably 0.5 to 5 weight percent and the polyvinylamine is present, on a solid basis, in the range of preferably 0.5 to 8 weight percent. In yet another embodiment, the additional polymer is a mixture of polyquaternium-6 and polyvinylamine wherein the polyquaternium-6 is present, on a solid basis, at a level of about 1.5 weight percent and the polyvinylamine is present, on a solid basis, 1 weight percent.

According to certain other embodiments of the invention, the additional polymer is added at between 35° C. and 55° C.

Core/Active Materials.

The core of the microcapsules of the invention can include one or more active materials including, but not limited to, flavors and/or fragrance ingredients such as fragrance oils. Individual perfume ingredients that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2, 2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha,3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert.-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert.-butyl-(2,4-dimethyl-3-cyclohexen-1-yl)ketone;

xv) esters of cyclic alcohols, such as, for example, 2-tert.-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert.-butylphenyl)propanal, 3-(4-tert.-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert.-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methy-N-methylanthranilate, Schiff's bases of methyl anthranilate with 7-hydroxy-3,7-dimethyloctanal, 2-methyl-3-(4-tert.-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, Litsea cubeba oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated fragrance oil is from about 80% to about 5% of the total capsule suspension, preferably from about 60% to about 10% of the total capsule suspension, and most preferably from about 50% to about 20% of the total capsule suspension.

In addition to the fragrance materials, the present invention also contemplates the incorporation of other core additives including solvent, emollients, and core modifier materials encapsulated by the encapsulating polymer.

The present invention also contemplates the incorporation of solvent materials, particles or polymeric core modifiers into the core. The solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater that 10. Suitable materials include, but are not limited to triglyceride oil, mono and diglycerides, mineral oil, silicone oil, diethyl phthalate, polyalpha olefins, castor oil and isopropyl myristate. In a highly preferred embodiment the solvent materials are combined with fragrance materials that have high Clog P values as set forth above. It should denoted that selecting a solvent and fragrance with high affinity for each other will result in the most pronounced improvement in stability. This specific affinity may be measured by determining the Solvent-Water partition coefficient for the fragrance material. Appropriate solvents include, but are not limited to, mono-, di- and tri-esters, and mixtures thereof, of fatty acids and glycerine. The fatty acid chain can range from C4-C26. Also, the fatty acid chain can have any level of unsaturation. For instance capric/caprylic triglyceride known as NEOBEE M5 (Stepan Corporation). Other suitable examples are the CAPMUL series by Abitec Corporation, for instance CAPMUL MCM. Isopropyl myristate fatty acid esters of polyglycerol oligomers include $R_2CO-[OCH_2-CH(OCOR_1)-CH2O-]_n$, where $R_1$ and $R_2$ can be H or C4-26 aliphatic chains, or mixtures thereof, and n ranges between 2-50, preferably 2-30. Nonionic fatty alcohol alkoxylates like the NEODOL surfactants by BASF, the DOBANOL surfactants by Shell Corporation or the BIOSOFT surfactants by Stepan, wherein the alkoxy group is ethoxy, propoxy, butoxy, or mixtures thereof. In addition, these surfactants can be end-capped with methyl groups in order to increase their hydrophobicity. Di- and tri-fatty acid chain containing nonionic, anionic and cationic surfactants, and mixtures thereof are also contemplated, as are fatty acid esters of polyethylene glycol, polypropylene glycol, and polybutylene glycol, or mixtures thereof. Polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; and di-isodecyl adipate can also be included. In certain embodiments, ester oils have at least one ester group in the molecule. One type of common ester oil useful in the present invention are the fatty acid mono and polyesters such as cetyl octanoate, octyl isononanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), magenase (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

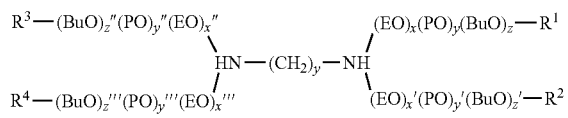

where $R^1$, $R^2$, $R^3$, and $R^4$ are independently H or any alkyl or fatty alkyl chain group. Examples of such polymers are the commercially known as TETRONICS by BASF Corporation.

Sacrificial core ingredients can also be included. These ingredients are designed to be lost during or after manufacture and include, but are not limited to, highly water soluble or volatile materials.

The level of solvent materials, particles or polymeric core modifiers in the core encapsulated by the encapsulating polymer should be greater than about 10 weight percent, preferably greater than about 30 weight percent and most preferably greater than about 70 weight percent. In addition to the solvent, it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of high Clog P fragrance chemicals will likely require a lower level of hydrophobic solvent than fragrance chemicals with lower Clog P to achieve similar performance stability. As those with skill in the art will appreciate, in a highly preferred embodiment, high Clog P fragrance chemicals and hydrophobic solvents comprise greater than about 80, preferably more than about 90 and most preferably greater than 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

Cationic Deposition Aids.

Cationic deposition aids can also be used to aid in deposition of capsules to surfaces such as fabric, hair or skin. These include but are not limited to cationically charged water-soluble polymers which can be applied to the fragrance encapsulated polymer. This water-soluble polymer can also be an amphoteric polymer with a ratio of cationic and anionic functionalities resulting in a net total charge of zero and positive, i.e., cationic. Those skilled in the art would appreciate that the charge of these polymers can be adjusted by changing the pH, depending on the product in which this technology is to be used. Any suitable method for coating the cationically charged materials onto the encapsulated fragrance materials can be used. The nature of suitable cationically charged polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool) is used the cationic polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein, molecular weight is provided as weight average molecular weight. Optionally, these cationic polymers can be used in combination with nonionic and anionic polymers and surfactants, possibly through coacervate formation.

Particular examples of polymers that can be used to coat the encapsulated fragrance include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDADMAC on cellulose, e.g., CELQUAT L-200 (POLYQUATERNIUM-4), POLYQUATERNIUM-10 and POLYQUATERNIUM-24, commercially available from National Starch, Bridgewater, N.J. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

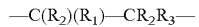

wherein, $R_1$ is any alkane from C1-C25 or H, wherein the number of double bonds ranges from 0-5, $R_1$ is an alkoxylated fatty alcohol with any alkoxy carbon-length of C1-C25, or $R_1$ is a liquid crystalline moiety that can provide the polymer with thermotropic liquid crystalline properties $R_2$ is H or $CH_3$; and $R_3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

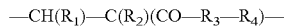

wherein, $R_1$ is any alkane from C1-C25 or H with number of double bonds from 0-5, $R_1$ is an alkoxylated fatty alcohol with a C1-C25 alkyl chain length, or $R_1$ is a liquid crystalline moiety that provides the polymer with thermotropic liquid crystalline properties;

$R_2$ is H or $CH_3$;

$R_3$ is a C1-25 alkyl alcohol or an alkylene oxide with any number of double bonds, or $R_3$ may be absent such that the C=O bond is (via the C-atom) directly connected to $R_4$; and $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —$OR_1$, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAFQUAT HS100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. Nos. 4,395,541 and 4,597,962;

iii) adipic acid/dimethyl amino hydroxypropyl diethylene triamine copolymers, such as CARTARETIN F-4 and F-23, commercially available from Sandoz;

iv) polymers of the general formula: —[N(CH$_3$)$_2$—(CH$_2$)$_x$—NH—(CO)—NH—(CH$_2$)$_y$—N(CH$_3$)$_2$)—(CH$_2$)$_z$—O—(—CH$_2$)$_p$]$_n$—, with x, y, z, p=1-12, and n according to the molecular weight requirements. Examples are Polyquaternium 2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: —Si(R$_1$)(R$_2$)—O≠]$_x$—[Si(R$_3$)(R$_2$)—O—]$_y$,— where R$_1$ is any alkane from C1-C25 or H with number of double bonds from 0-5, aromatic moieties, polysiloxane grafts, or mixtures thereof. $R_1$ can also be a liquid crystalline moiety that can provide the polymer with thermotropic liquid crystalline properties. $R_2$ can be H or CH$_3$; and $R_3$ can be —$R_1$—$R_4$, where $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, —COOH, —COO— alkali salt, any C1-25 alcohol, —C(O)—$NH_2$ (amide), —C(O)—N(R$_2$)(R$_2$') (R$_2$"), sulfobetaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-$R_5$ or naphthalene-$R_6$ where $R_5$ and $R_6$ are $R_1$, $R_2$, $R_3$, sulfonic acid or its alkali salt or organic counter ion. $R_3$ can also be —(CH$_2$)$_x$—O—CH$_2$—CH(OH)—CH$_2$—N(CH$_3$)$_2$—CH$_2$—COOH and its salts. Any mixture of these $R_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent EP0737183B1.

Furthermore, copolymers of silicones and polysaccharides and proteins can be used (e.g., those commercially available as CRODASONE brand products).

Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazinealkylene main chain copolymers disclosed by Kashiki and Suzuki (1986) *Ind. Eng. Chem. Fundam.* 25:120-125.

As indicated, the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion.

In accordance with the compositions and methods disclosed herein, the wall polymer level of the polyurea capsules can be from about 5 to about 0.1% of the total capsule suspension, from about 2.5 to about 0.1% of the total capsule suspension, from about 2.0 to about 0.5% of the total capsule suspension, or from about 1.5 to about 1% of the total capsule suspension. In other embodiments, the wall polymer level is from about 15 to about 0.1% of the total capsule suspension, preferably from about 10 to about 1% of the total capsule suspension, or most preferably from about 5 to about 2% of the total capsule suspension.

In a further embodiment of the invention, the amount of encapsulated active material is from about 80 to about 5% of the total capsule suspension, preferably from about 60% to about 10% of the total capsule suspension, or most preferably from about 50 to about 20% of the total capsule suspension.

In one embodiment of the method, the cross-linking agent is a polyamine, wherein the stoichiometry of the polyamine and polyisocyanate can be manipulated to give reduced amounts of polyisocyanate in the prepared capsule slurry. The stoichiometry of the polyamine to isocyanate will vary from 1 to 1, (one amine group per one isocyanate group), preferably from 2 to 1, (two amine groups per one isocyanate group), and most preferably from 4 to 1 (four amine groups per one isocyanate group).

In certain embodiments of the invention, the capsule slurry is cured at a temperature greater than about 55° C.; greater than about 65° C.; greater than about 75° C.; greater than about 85° C.; greater than about 95° C.; greater than about 105° C. or greater than 120° C.

Microcapsules prepared in accordance with this invention preferably have a size in the range of from 0.1 to 100 microns, or preferably from 0.2 to 50 microns depending on the emulsifier and shear rates used.

Applications.

The present invention is well-suited for use in formulations containing water or a combination of water and alcohol, e.g., ethanol and isopropanol. Therefore, the present invention includes formulations containing the purified polyurea capsules in a variety of products including hydroalcoholic products, fine fragrance products; eau de toilettes; leave-on personal care applications including hair refreshers, aerosol hair sprays and lotions; liquid and powder detergents; rinse conditioners; personal care products including shampoos, conditioners, and personal washes; personal cleaners and sanitizers; fabric care products such as fabric refreshers; and industrial and personal cleaners. Especially preferred consumer products that use the capsules of the invention include, without limitation, personal care products such as such as shampoos, rinses, hair conditioners, creams, body washes and the like; and laundry products such as laundry detergents, fabric softeners, bleaches, brighteners and fabric rinse conditioners, e.g., for high efficiency front load washing machines (e.g., those manufactured by Miele, Germany); cleaning products and the like. Rinse off products may be liquids, solids, pastes, or gels, of any physical form. Also included in the use of the microcapsules are applications where a second active ingredient is included to provide additional benefits for an application. The additional beneficial ingredients include fabric softening ingredients, skin moisturizers, sunscreen, insect repellent and other ingredients as may be helpful in a given application. Also included are the beneficial agents alone, that is without the fragrance.

Capsules having a polyurethane or polyurea capsule wall are very suitable to carry a variety of hydrophobic or hydrophilic benefit agents to be used in products for application to all kinds of surfaces. On the one hand surfaces may be inanimate, such as hard surfaces found in and around the house, e.g., wooden, metal, ceramic, glass and paint surfaces, or soft surfaces such as clothing, carpets, curtains and other textiles. On the other hand, such surfaces may be animate surfaces, more particularly surfaces of a human or animal body, i.e., human or animal skin and hair. For the purposes of this invention animate surfaces do not include plant surfaces.

Products intended for application to a surface are generally intended for washing/cleaning or for caring/protecting or both. Examples are cleaning products for hard surfaces or textiles, caring/protection products like polishes and waxes for delicate surfaces such as wood, car paint and leather, laundry softening agents, anti-soiling agents, water repelling agents, and the like. Examples of products intended for the human skin are bath and shower products and shampoo for skin and hair cleansing, and all kinds of skin and hair care/protection products such as hair conditioners, hand and body lotions and creams, lip care products, deodorants and antiperspirants, make up products and the like.

The dosage of the microcapsules in the rinse off products is from about 0.05 weight percent to 10 weight percent, preferred 0.2 weight percent to about 5 weight percent, and most preferred 0.5 weight percent to about 2 weight percent.

Cleaning and cleansing compositions will include one or more surfactants that may be chosen from anionic, cationic, nonionic, zwitterionic and amphoteric surfactants known in the art. For cleansing composition for skin or hair the surfactants must obviously meet the condition of being suitable for topical application.

The compositions according to the invention may optionally include a variety of components known in the art and adapted to their specific use. Thus, compositions intended for inanimate surfaces may include components such as builders, sequestrants, hydrotropes, organic solvents, pH regulation components such as organic or inorganic acids and/or bases, thickening agents, chlorine or peroxide bleaches, laundry softening agents, scouring agents, biocides, coloring agents, pearlescent, preservatives, perfumes. Compositions intended for application may contain a variety of vehicles suitable for topical application and a variety of benefit agents for skin or hair.

As described herein, the purified polyurea capsules of the invention are well-suited for use in a variety of well-known household products such as laundry detergent and fabric softeners, liquid dish detergents, automatic dish detergents, bathroom cleaners, bath tissue, tumble dryer sheets, rug deodorizers, candles, floor cleaners, disinfectants, window cleaners; household devices such as paper towels, disposable wipes, room deodorizers; baby care products such as diaper rash cream/balm or baby powder; baby care devices such as diapers, bibs and wipes; health care devices such as dental floss, toothbrushes, tampons and feminine napkins; personal care products such as personal cleansers (e.g., bar soap or body wash), sunscreen (spray or lotion), wax-based deodorant, glycol/soap-type deodorant, lotion, body powder, shaving cream, bath soak, exfoliating scrub; personal care devices such as facial tissues, and cleansing wipes; hair care products such as shampoo (liquid or dry powder), hair conditioner (rinse out or leave-in), hair fixative or style aids, hair bleaches, dyes or colorants; and beauty care products such as fine fragrances, solid perfume, liquid or powder foundation, eye shadow, and lipstick/lip balm. Given their particular use in hydroalcoholic medium, the purified polyurea capsules of this invention find particular application in personal care products, a fine fragrance or Eau De Toilette product, or a deodorant, roll-on or aerosol product.

These products can employ surfactant and emulsifying systems that are well-known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, and 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818.

Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Toothpastes and other oral care products that can employ the present invention include those described in U.S. Pat. Nos. 6,361,761, 6,616,915, 6,696,044, 6,193,956, 6,132,702, 6,004,538, 5,939,080, 5,885,554, 6,149,894, 5,505,933, 5,503,823, 5,472,685, 5,300,283 and 6,770,264.

Personal care products, including cosmetic or pharmaceutical preparations can be formulated as "water-in-oil" (W/O) type emulsions, "oil-in-water" (O/W) type emulsions or as multiple emulsions, for example of the water-in-oil-in-water (W/O/W) type, as a PIT emulsion, a Pickering emulsion, a micro-emulsion or nano-emulsion. Emulsions that are particularly preferred are of the "oil-in-water" (O/W) type or water-in-oil-in-water (W/O/W) type.

As used herein stability of the products is measured at room temperature or above over a period of at least a week. More preferably the capsules of the present invention are allowed to be stored at room temperature for more than about two weeks and preferably more than about a month.

These and additional modifications and improvements of the present invention may also be apparent to those with ordinary skill in the art. The particular combinations of elements described and illustrated herein are intended only to represent only a certain embodiment of the present invention and are not intended to serve as limitations of alternative articles within the spirit and scope of the invention. As used herein all percentages are weight percent unless otherwise noted, ppm is understood to stand for parts per million, mL is understood to be milliliter, g is understood to be gram, and mol is understood to be mole. All materials are reported in weight percent unless noted otherwise. As used herein all percentages are understood to be weight percent. The abbreviations PU stand for polyurea; CMC stands for carboxymethyl cellulose; PQ6 is polyquaternium-6 available as MERQUAT 100 (Nalco); LUPAMIN 9095 (BASF) is polyvinylamine; LUPASOL G20 and LUPASOL SK (BASF) are polyethylene imine; PQ22 is polyquaternium-22 available as MERQUAT 280 (Nalco); PQ39 is polyquaternium-39 available as MERQUAT Plus 3330 (Nalco); PQ47 is polyquaternium-47 available as MERQUAT 2001 (Nalco); CI Starch is cationic starch available as CHARGEMASTER L340 (Grain Processing Corporation).

The invention is described in greater detail by the following non-limiting examples.

Example 1: Polyurea Capsule Composition

Preparation of Sample 1.

Ninety-six grams of a fragrance, Apple (International Flavors and Fragrance, Union Beach, N.J.) was weighed out and combined with 24 g of NEOBEE oil (Stepan, Chicago, Ill.) and 9.6 g of isocyanate monomer, LUPRANATE M20 (BASF corporation, Wyandotte, Mich.) to form the oil phase. In a separate beaker, a 1% surfactant solution (160 g) was prepared by dissolving sufficient amount of MORWET D-425 (Akzo Nobel, Fort Worth, Tex.) in deionized (DI) water. The oil phase was then emulsified into the aqueous phase to form the fragrance emulsion under shearing (ULTRA TURRAX, T25 Basic, IKA WERKE) at 6500 rpm for two minutes.

The fragrance emulsion was placed in a round bottom vessel and 10.8 g of 40% hexamethylene diamine (HMDA) (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

Preparation of Sample 2. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, LUPRANATE M20 (BASF corporation, Wyandotte, Mich.) to form the oil phase. In a separate beaker, a solution (160 g) containing 1% MORWET D-425 (Akzo Nobel, Fort Worth, Tex.) was used as the aqueous phase. The oil phase was then emulsified into the aqueous phase to form the fragrance emulsion under shearing (ULTRA TURRAX, T25 Basic, and IKA WERKE) at 6500 rpm for two minutes.

The fragrance emulsion was placed in a round bottom vessel and 10.8 g of 40% HMDA (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

After capsule preparation, the capsule slurry was washed with DI water using a separatory funnel. Specifically, 300 mL DI water was mixed with 300 g capsule slurry in a 1000 mL separatory funnel. The funnel was then sealed and shaken gently and was allowed to sit overnight so the capsule slurry separated from DI water. The water layer was then removed. This process was repeated several times until the pH of the slurry was 7.0. Analytical measurement indicated the concentration of HMDA is less than 0.05%.

While 9.6 g of LUPRANATE M20 was used in this example, the amount of LUPRANATE M20 can be varied from 9.6 to 28.8 g, with the addition of corresponding amount of 40% HMDA solution (10.8 g to 32.4 g). Likewise, the amount of MORWET D-425 can be varied from 0.5 to 4% depending on formulation need. Moreover, other dispersants include PVA (polyvinyl alcohol), CMC (carboxymethyl cellulose), PSSS (polystyrene sulfonic acid, sodium salt) can be employed.

Preparation of Sample 3. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, LUPRANATE M20 (BASF corporation, Wyandotte, Mich.) to form the oil phase. In a separate beaker, a solution (160 g) containing 1% MORWET D-425 (Akzo Nobel, Fort Worth, Tex.) was used as the aqueous phase. The oil phase was then emulsified into the aqueous phase to form the fragrance emulsion under shearing (ULTRA TURRAX, T25 Basic, and IKA WERKE) at 6500 rpm for two minutes.

The fragrance emulsion was placed in a round bottom vessel and 10.8 g of 40% HMDA (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

After preparation, the capsule slurry was washed with 1M NaCl aqueous solution using a separatory funnel. Specifically, 300 mL 1M NaCl aqueous solution was mixed with 300 g capsule slurry in a 1000 mL separatory funnel. The funnel was then sealed and shaken gently and was allowed sit overnight so that the capsule slurry could separate from the aqueous solution. The aqueous layer was then removed. This process was repeated several times until the pH of the slurry was 7.0. The capsule slurry was further washed with DI water several times using a separatory funnel.

Example 2: Sensory Performance of Polyurea Capsules

To establish the consumer benefit of the polyurea capsules, Sample 1 as prepared in Example 1 was incorporated into an aerosol formulation. The composition of the aerosol is provided in Table 1.

TABLE 1

| Raw Material | Description | % |
| --- | --- | --- |
| A46 | Propellant(Butane/Isobutane Mix) | 53.8 |
| Alcohol | Diluent | 44 |
| Fragrance | Perfume | 1.4 |
| Propylene Glycol | Solubilizer | 0.6 |
| COSMOCIL CQ | Deodorant Active | 0.2 |

A technician applied (sprayed) 1.0 g of each aerosol formulation onto a fragrance wearer's upper forearm. Eight arms were tested per sample using 15 trained judges. The judges rated the intensity of the product on skin at 5 hours after application under two conditions, prior to activation (pre-rub) and again in post-rubbed condition. For the post-rub evaluation, each wearer gently rubbed the upper forearm up and down to a count of six with two fingers. Judges smelled the top part of the forearm when evaluating the sample. Two-way analysis of variance was conducted with sample and panelists as independent variables and intensity as dependant variable, and again with condition (pre and post) and panelists as independent variables and intensity as dependant variable. Post hock analysis was by Duncan Multiple Comparison with significance set at 95% CI.

The sensory results are given in FIG. 1. This analysis indicated that the polyurea capsules provided significantly greater fragrance intensity at all-time points compared to neat fragrance. Moreover, the polyurea capsules had a significant increase in fragrance intensity from pre to post evaluation.

Example 3: Sensory Performance of Purified Polyurea Capsules

Figure 2:
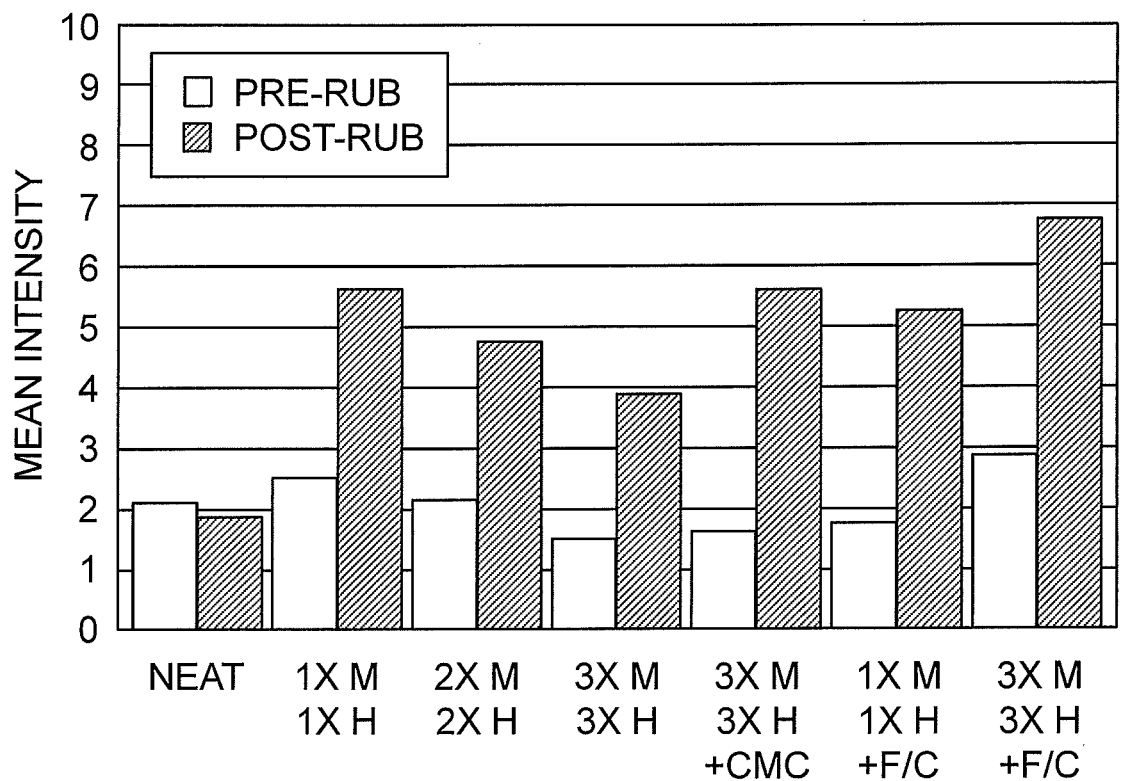
FIG. 2 shows sensory performance of polyurea capsules in hydroalcoholic medium (80:20 EtOH:$H_2O$) as compared to neat fragrance. Capsules were composed of 9.6 g (1× M), 19.2 g (2× M) or 28.8 g (3× M) LUPRANATE M20; or 10.8 g (1 × H), 21.6 g (2× H) or 32.4 g (3× H), with (+) or without (−) CMC or FLEXAN/CMC (F/C). All samples were purified and had a pH of 7.

To establish the consumer benefit of the purified polyurea capsules, polyurea capsules prepared in accordance with Sample 2 in Example 1 was mixed into a hydroalcoholic solution that contained 80% ethanol and 20% water. The concentration of the capsules was 4.5%. The polyurea capsule solution (0.3 g) was then sprayed onto a blotter (4×6) and allowed to dry overnight before being evaluated by a panel of 12 judges. The fragrance intensity was rated on a scale ranging from 0 to 10. A numerical value of 10 would suggest the subject generated a strong smell. The results are shown in FIG. 2.

Figure 3:
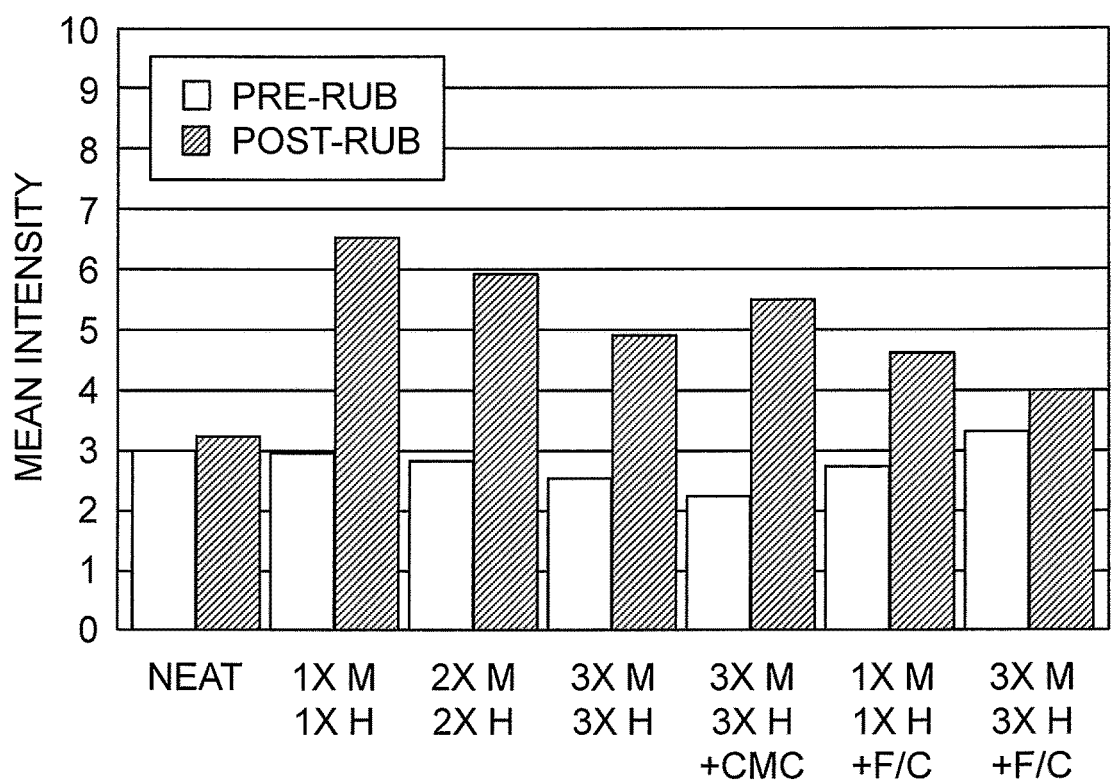
FIG. 3 shows sensory performance of polyurea capsules of FIG. 2 in hydroalcoholic medium after being aged at 25° C. for 4 weeks.

The results of this analysis indicated that capsules prepared in accordance with the present invention had a much stronger fragrance intensity compared to neat fragrance in the post-rubbing stage and were able to deliver the full benefit of the fragrance formulation. Moreover, the sensory performance of the polyurea capsules was retained after the samples were aged at 25° C. for 4 weeks (FIG. 3), demonstrating the robust storage stability and performance of the capsules.

What is claimed is:

1. A capsule composition comprising a capsule having an encapsulating polymer and an active material encapsulated by the encapsulating polymer,
   wherein the active material is present at a level of 10% to 60%;
   the encapsulating polymer is the reaction product of polymerization between at least one polyisocyanate and a cross-linking agent in the presence of a capsule formation aid;
   the polyisocyanate is present at a level of 1% to 7.5%;
   the cross-linking agent is hexamethylenediamine or polyethyleneimine present at a level of 0.1 to 5%;
   the capsule formation aid is present at a level of 0.5% to 4% and is (i) a mixture of sulfonated polystyrene and cetyl trimethyl ammonium chloride, (ii) a mixture of sulfonated polystyrene, cetyl trimethyl ammonium chloride and carboxymethyl cellulose, iii) a mixture of sulfonated polystyrene and carboxymethyl cellulose, (iv) a mixture of carboxymethyl cellulose and polyvinylpyrrolidone, or (v) a mixture of polyvinyl alcohol and polyvinylpyrrolidone; and
   all percentages are based on the weight of the capsule composition.

2. The capsule composition of claim 1, wherein the carboxymethyl cellulose is present at a level of 0.1% to 2%.

3. The capsule composition of claim 1, wherein the active material is a fragrance.

4. The capsule composition of claim 1, wherein the polyisocyanate contains xylylene diisocyanate, diphenylmethane diisocyanate, or a combination thereof.

5. The capsule composition of claim 1, wherein the cross-linking agent is hexamethylenediamine.

6. The capsule composition of claim 1, wherein the cross-linking agent is polyethyleneimine.

7. The capsule composition of claim 1, wherein the capsule formation aid is a mixture of the sulfonated polystyrene and the cetyl trimethyl ammonium chloride.

8. The capsule composition of claim 1, wherein the capsule formation aid is a mixture of the sulfonated polystyrene, the cetyl trimethyl ammonium chloride, and the carboxymethyl cellulose.

9. The capsule composition of claim 1, wherein the capsule formation aid is a mixture of the sulfonated polystyrene and the carboxymethyl cellulose.

10. The capsule composition of claim 1, wherein the capsule formation aid is a mixture of the carboxymethyl cellulose and the polyvinylpyrrolidone.

11. The capsule composition of claim 1, wherein the capsule formation aid is a mixture of the polyvinyl alcohol and the polyvinylpyrrolidone.

12. A consumer product comprising the capsule composition of claim 1.

13. The consumer product of claim 12, wherein the consumer product is a shampoo, a hair conditioner, a soap, a body wash or other hygiene product, a cosmetic preparation, a body liquid detergent, an all-purpose cleaner, a fabric softener or refresher, an ironing water or a detergent, softener or drier sheet, a fine fragrance or Eau De Toilette product, a deodorant, or a roll-on or aerosol product.

* * * * *